United States Patent [19]
Müller

[11] Patent Number: 5,674,225
[45] Date of Patent: Oct. 7, 1997

[54] EXTRACTION TOOL FOR A SHAFT OF A HIP JOINT PROSTHESIS OR OF A CORRESPONDING RASP

[75] Inventor: Stephan Müller, Thun, Switzerland

[73] Assignee: Protek AG, Muensingen-Bern, Switzerland

[21] Appl. No.: 785,565

[22] Filed: Jan. 21, 1997

Related U.S. Application Data

[63] Continuation of Ser. No. 421,127, Apr. 12, 1995, abandoned.

[30] Foreign Application Priority Data

Apr. 25, 1994 [EP] European Pat. Off. .......... 94810226

[51] Int. Cl.⁶ .................................................. A61B 17/56
[52] U.S. Cl. .................................. 606/99; 606/100
[58] Field of Search ........................... 606/100, 99, 86, 606/102, 91, 85, 89; 623/22, 23

[56] References Cited

U.S. PATENT DOCUMENTS

| | | |
|---|---|---|
| 3,857,389 | 12/1974 | Amstutz . |
| 4,686,971 | 8/1987 | Harris . |
| 4,919,153 | 4/1990 | Chin ............................. 606/93 |
| 4,993,410 | 2/1991 | Kimsey ....................... 606/100 |
| 5,064,427 | 11/1991 | Burkinshaw ................. 606/99 |
| 5,350,381 | 9/1994 | Melton ........................ 606/85 |

FOREIGN PATENT DOCUMENTS

| | | |
|---|---|---|
| 0408102A1 | 1/1991 | European Pat. Off. . |
| 72.28530 | 4/1973 | France . |
| 2615097 | 11/1988 | France ........................ 606/99 |
| 2686016 | 7/1993 | France ........................ 606/99 |
| 2101002 | 5/1972 | Germany . |
| 9212846 U | 1/1993 | Germany . |
| WO91/06262 | 5/1991 | WIPO . |

*Primary Examiner*—Guy V. Tucker
*Attorney, Agent, or Firm*—Townsend and Townsend and Crew LLP

[57] ABSTRACT

The extraction tool comprises a sleeve part (13) which can be coupled to a neck portion (6) of a shaft which is to be withdrawn, and a coupling element (15) in the form of a collet which can be fitted onto the neck portion (6). The collet has an elongate section with wall segments (16a) which can be clamped against the neck portion (6), and comprises fittings (23) which can be guided into a constriction (24) of the neck portion (6), and a head part (17) which projects beyond the neck portion (6), wherein the head part (17) can be clamped against the sleeve part (13) via a bias screw (18). The coupling element (15) is loosely connected to the sleeve part (13) and fitted onto the neck portion (6). It can then be clamped by approaching the bias screw (16) against the sleeve part (13) and against the neck portion (6). A rigid yet easily releasable connection between the extraction tool and the shaft to be withdrawn is thus achieved in a simple manner.

14 Claims, 1 Drawing Sheet

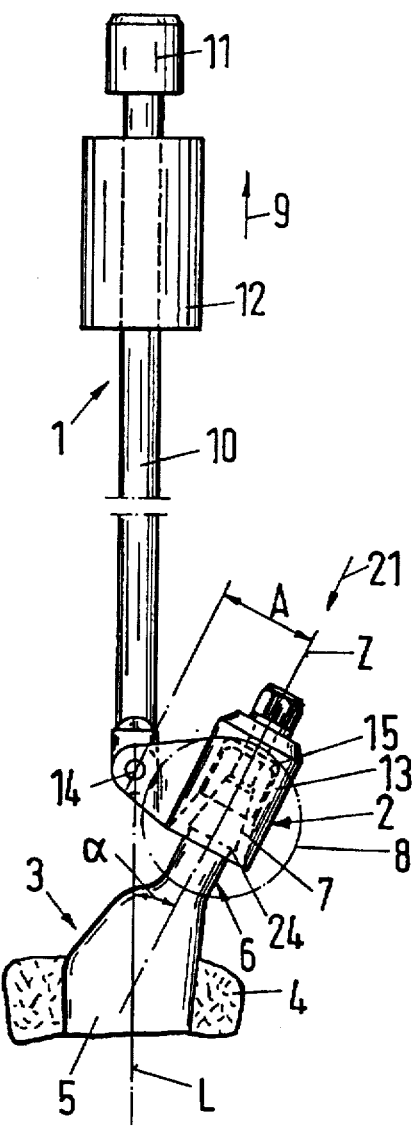
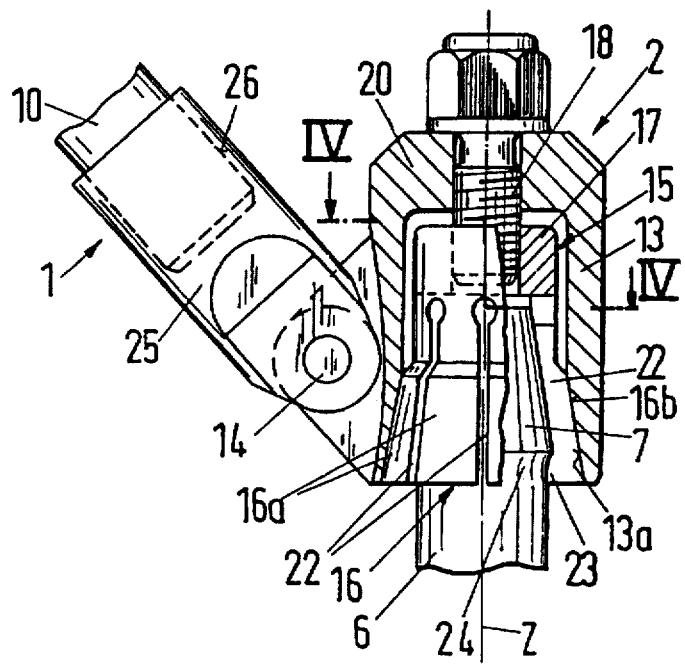
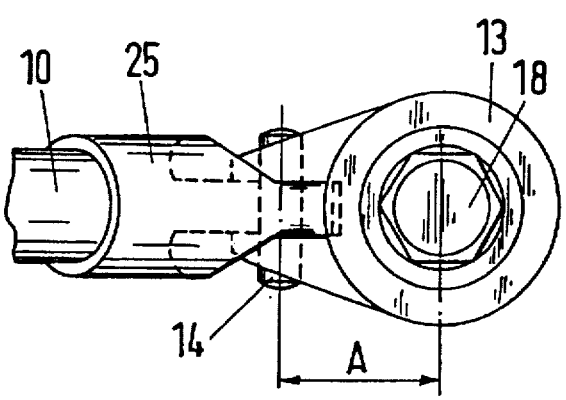
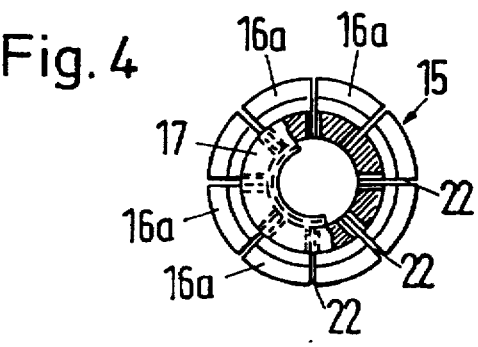

EXTRACTION TOOL FOR A SHAFT OF A HIP JOINT PROSTHESIS OR OF A CORRESPONDING RASP

This is a Continuation of application Ser. No. 08/421, 127, filed Apr. 12, 1995, now abandoned.

BACKGROUND OF THE INVENTION

The invention relates to an extraction tool for removing a shaft, of a femoral implant of a hip joint prosthesis, for example, from bone in which it is embedded.

An extraction tool of this kind is known from European patent application number 0 550 118 which comprises a holder rigidly connected to a grip part, with the holder including a ring-shaped driver which grips around a neck portion of the shaft which is to be withdrawn, and a pivot lever jointedly connected to the neck portion. The pivot lever can be clamped against the neck portion, which is surrounded by the ring-shaped driver, either via an adjustment part mounted displaceably on the grip part or via a rod assembly coupled to the grip part. The extraction tool has a plurality of movable parts which need to be adjusted relative to each other and which require a correspondingly large amount of time and effort for their manufacture and assembly, as well as for cleaning and sterilizing the tool.

It is an object of the invention to provide an improved extraction tool which, in comparison to previous embodiments, has a simplified, compact construction with a modest number of robust and easy-to-handle components which enable the tool and the implantation region to be kept clean with correspondingly little time and effort.

An advantage of the extraction tool of the invention is that the holder of the shaft of the prosthesis or of the rasp which is to be withdrawn grasps the end section of the neck portion receiving the head piece and thus acts at a position remote from the bone tissue so that the force to be applied to the shaft is transferred substantially in this end section at a distance from the bone tissue. The parts of the extraction tool are thus kept away from the bone tissue, which allows an unhindered view of the implantation region throughout. A further advantage of the extraction tool of the invention is that the sleeve part, which is placed onto the neck portion, together with the coupling element, forms a compact and simply actuatable holder. This makes it possible to accommodate the parts which are to be coupled together in a fully closed, cap-like housing. The apparatus of the invention has parts which are simple to manufacture, simple to put together and which can be easily cleaned and sterilized.

One embodiment of the invention makes it possible in a simple manner to establish and release a force-defined and shape-defined connection between the coupling element, which can be clamped against the neck portion, and the sleeve part, which can be clamped against the coupling element, in the direction of their common centering axis.

Another embodiment of the invention provides a particularly compact construction of the holder by forming the coupling element as a collet can be made from a relatively easily manufacturable turned piece which has relatively thin walls.

In another embodiment a snap connection is formed between the conical end section of the neck portion and the collet. The collet is displaceably, clampably held at the sleeve part and is fittable onto the neck portion in the axial direction. The snap connection thus formed is simple to establish (make) and release (break).

A further embodiment allows an adjustment of the handle part, or a corresponding connector part which can be coupled to different handle parts, which is independent of the working position of the holder. This makes it possible, within the limits set by anatomical factors, to transfer the forces to be applied to the shaft at different angular positions of the handle part.

An additional embodiment allows the transfer of the forces which are to be applied to the shaft along a line of action substantially congruent with a main axis of the shaft member, even though the forces act on the neck portion which is laterally offset from the shaft member.

BRIEF DESCRIPTION OF THE DRAWINGS

Further details and features are given in the following description of an embodiment of the invention which is shown in the drawings FIG. 1 is a side elevational view of an extraction tool of the invention for a shaft of an endoprosthesis;

FIG. 2 is a fragmentary view, partially in section, which shows parts of a corresponding extraction tool made according to another embodiment;

FIG. 3 shows the extraction tool of FIG. 2 in plan view; and

FIG. 4 is a detail, partially in section of the extraction tool shown in FIG. 2 and is taken along line IV—IV of FIG. 2.

DESCRIPTION OF THE PREFERRED EMBODIMENTS

The extraction tool of FIG. 1 comprises a handle part 1 and a holder 2 connected thereto. The holder can be coupled in a force-defined and shape-defined manner to a shaft 3 of a hip joint prosthesis. The shaft 3 comprises a shaft member 5 which can be inserted into a femur 4, and a neck portion 6 stepped laterally from the shaft member 5. The neck portion 6 is formed with an end section 7 which tapers conically relative to a centering axis Z. The centering axis Z is inclined at an angle alpha relative to the longitudinal axis L of the shaft member 5, as illustrated. The neck portion 6 serves as a fixing point for an artificial joint ball 8 which is shown in FIG. 1 with the dot-dashed line. The joint ball 8 is formed with a conical receiving bore matched to the end section 7. To allow the fitted position of the implant joint ball 8, and thus the center of rotation of the hip joint prosthesis, to be matched to the prevailing anatomical conditions, a number of joint balls 8 with receiving bores of different depths can be stocked in the known manner so that an appropriate joint ball can be selected and fitted onto the end section 7 in a self-locking manner.

Instead of the prosthesis shaft 3 illustrated, a rasp of corresponding shape and size can be provided which can be inserted into and withdrawn from the bone 4. A joint ball 8 can be fitted as a test ball onto the neck portion 7 of the rasp and can be brought together with a hip joint socket (not shown) in an exploratory fashion in order to establish the final position of the joint ball 8.

The handle part 1 comprises a guide rod 10 pivotably connected to a holder 2. At its free end, the guide rod 10 has an abutment 11 for a slide hammer 12 which is mounted displaceably on the guide rod 10. By moving the slide hammer 12 against the abutment 11, a force suitable for withdrawing a particular shaft 3 can be transmitted in the known manner via the guide rod 10 and holder 2 to the shaft member 5. It is this force which knocks the shaft member 5 out of the bone tissue. As can be seen, in particular from FIG. 2, the holder 2 has a bell-like sleeve part 13 which can be fitted onto the neck portion 6 and which is pivotably coupled with the guide rod 10 via a spigot 14. The holder 2 also has a coupling element 15 in the form of a collet which can be inserted into the sleeve part 13 and fitted onto the end section 7 of the neck portion 6. The coupling element 15 is formed with a side wall 16 surrounding the end section 7 and a head piece 17 which projects beyond the end section 7. The head piece 17 can be held clamped against a corresponding head part 20 of the sleeve part 13 by means of a central bias screw 18. The side wall 16 is formed by an elongate section which can be fitted onto the end section 7 of a correspondingly conical inner surface. The elongate section is subdivided into a number (eight in FIG. 4) of radially displaceable tongue-like wall segments 16a via open, longitudinal slots 22 which extend in the fitment direction (arrow 21). Each of these wall segments is resiliently biasable against the end section 7.

As can also be seen from FIG. 2, each of the wall segments 16a can be provided at their free ends with an inwardly projecting, bead-like fitting part 23. The fitting parts 23 are formed in such a manner that, when the coupling part 15 is fitted onto the end section 7, they clip into a cut-back constriction 24 of the neck portion 6 which adjoins the end section 7. The fitting parts 23 thus form abutment parts which can be engaged with and disengaged from the constriction. It is these fitting parts which transmit the tensile forces necessary for knocking out the shaft member 5 to the neck portion 6.

As shown in FIG. 2, the end parts of the side wall 16 of the coupling element 15 can be realized with a conical outer surface 16b which diverges in the fitment direction (arrow 21). The outer surface 16b is designed so that it can be brought together with a correspondingly conical inner surface 13a of the sleeve part 13. The resultant connection can be self-locking. The coupling element 15 loosely connected to the sleeve part 13 can be slid onto the end section 7 of the neck portion 6 until the fitting parts 23 snap into the constriction 24 and, subsequently, can be clamped by tightening the bias screw 18 against the inner surface 13a and the end section 7. A connection between the holder 2 and the shaft 3 is thus formed which is rigid in the direction of the centering axis Z but which is easy to release.

As shown in FIG. 1, the hinge position formed at the sleeve part 13 can be arranged at a lateral distance from the centering axis Z such that, when the sleeve part 13 is fitted onto the neck portion 6, the spigot 14 lies substantially in an extension of the longitudinal axis L of the shaft member 5. The line of action of the force to be transferred in the particular case to the shaft 3 is thus coincident with this longitudinal axis L.

Referring to FIGS. 2 and 3, the hinge position provided at the handle part 1 for the holder 2 can be formed at a connector piece 25. The connector piece 25 can be coupled either with the guide rod 10 or with a corresponding grip part. As illustrated, the connector part 25 comprises a threaded coupling sheath for receiving a threaded section 26 of the guide rod 10, the threads being compatible with each other.

Numerous modifications are possible within the scope of the invention. For example, the sleeve part 13 can be rigidly connected to the handle part 1 or to the connector part 25. The sleeve part 13 and the coupling element 15 can be formed with cylindrical guide surfaces at their end parts which are to be brought together. The coupling element 15 can also be formed with a cylindrical inner surface which can be fitted onto a cylindrical end section of a corresponding neck portion. Instead of the illustrated collet, a different coupling arrangement could be provided, for example in the form of loose carrier elements arranged in a corresponding sleeve part which could be clamped against the neck portion 6. Furthermore, the holder 2 of the invention could also be mounted onto, or coupled to a handle part (not shown) of a device for knocking the shaft 3 into the bone 4.

In summary, the invention can be described as follows:

The extraction tool comprises a sleeve part 13 which can be coupled to a neck portion 6 of a shaft which is to be withdrawn, and a coupling element 15 in the form of a collet which can be fitted onto the neck portion 6. The collet has an elongate section with wall segments 16a which can be clamped against the neck portion 6, and comprises fittings 23 which can be guided into a constriction 24 of the neck portion 6, and a head part 17 which projects beyond the neck portion 6, wherein the head part 17 can be clamped against the sleeve part 13 via a bias screw 18. The coupling element 15 is loosely connected to the sleeve part 13 and fitted onto the neck portion 6. It can then be clamped by tightening the bias screw 16 against the sleeve part 13 and against the neck portion 6. A rigid yet easily releasable connection between the extraction tool and the shaft to be withdrawn is thus achieved in a simple manner.

What is claimed is:

1. An extraction tool for a shaft having a shaft member which can be inserted into and withdrawn from a bone and a neck portion including a recess spaced from a free end of the neck portion, the extraction tool comprising a handle part, a holder including a sheath portion and a coupling element, the sheath portion being placeable on the neck portion and having a bore for at least partly receiving the neck portion, the coupling element being supported by the sheath portion and being clampable against the neck portion, and a fitting attached to the coupling element which is engageable with and disengageable from the recess in the neck portion, wherein the sheath portion comprises a sleeve disposed about the coupling element and movable relative thereto in an axial direction of the neck portion, and wherein the sleeve and the coupling element have cooperating guide surfaces at least one of which diverges in the axial direction from the free end of the neck portion towards the recess and wherein the extraction tool further comprises means for moving the sleeve relative to the coupling element for clamping the sheath portion against the neck portion.

2. Extraction tool according to claim 1 wherein the coupling element comprises a collet at least partially insertable into the sleeve and which includes a tubular section for positioning on the neck portion and divided into a plurality of radially displaceable tongue segments by spaced-apart, longitudinal slots which extend in the axial direction, the collet including a head part connecting first ends of the tongue segments, and the means for moving a threaded connection between the sleeve and the head part for moving the sleeve and the collet relative to each other.

3. An extraction tool according to claim 2 wherein the neck portion includes a conical end section and the recess is an undercut formed by an end of the conical end section, wherein the collet includes a conical inner surface defined by axially tapered surfaces of the tongue segments for placement over the conical end section, and wherein the fitting comprises radially inwardly oriented projections proximate ends of the tapered surfaces of the tongue segments for engaging the undercut.

4. An extraction tool according to claim 1 including hinge means for pivotally connecting the handle part with the holder.

5. An extraction tool according to claim 4 wherein the shaft and the neck portion each have a longitudinal axis, the axes being angularly inclined with respect to each other, and wherein the hinge means include positioning means operatively coupled with the holder and the handle part for locating a pivot axis of the hinge means at least approximately at an extension of a longitudinal axis of the shaft member when the coupling element and the sheath are placed on the neck portion.

6. Apparatus for extracting an elongated member from a bone cavity in which the member is disposed, the member including a neck protruding from the bone along an axis of the neck, terminating in an end, and having an undercut spaced from the end, the apparatus comprising a coupling element having a bore for placement over the neck and including a fitting shaped to engage the undercut when at least a portion of the neck is disposed in the bore; securing means operatively coupled with the fitting for extending the fitting into the undercut in response to relative motion, the relative motion occurring between the neck and at least one of the coupling element and the securing means in the direction of the axis of the neck; and a handle connected with the coupling element for applying a force to the member for loosening the member in and withdrawing it from the bone.

7. Apparatus according to claim 6 wherein the member comprises a hip joint prosthesis.

8. Apparatus according to claim 6 wherein the member comprises a bone rasp.

9. Apparatus according to claim 6 wherein the securing means is defined by the coupling element and comprises a tubular member which defines the bore and adapted to overlie the neck and an end member from which the tubular member depends, and a plurality of slits in the tubular member extending from an end of the tubular member towards the end member which define a plurality of flexible tongues, and wherein the fitting comprises projections adjacent free ends of the tongues.

10. Apparatus according to claim 9 wherein the securing means includes ring means disposed about the tongues, movable relative to the coupling element in the axial direction and engaging the tongues for forcing the projections into the undercut.

11. Apparatus according to claim 6 wherein the coupling element includes at least one radially displaceable member which carries the fitting, and wherein the securing means comprises a sleeve surrounding the coupling element, engaging the displaceable member and movable relative thereto in the axial direction for generating a force which retains the fitting in the undercut.

12. Apparatus according to claim 6 including means for pivotally connecting the handle with the coupling element.

13. Apparatus for pulling a shaft embedded in a bone and having a portion which projects out of the bone in an axial direction, terminates in a free end, and has an undercut spaced from the free end; a collet having an undivided head part, an elongated, tubular section extending from the head part for placement over at least part of the projecting portion of the shaft, the tubular section including a plurality of axially oriented slits to define a plurality of radially displaceable tongue segments, radially inwardly oriented projections proximate ends of the tongue segments shaped to engage the undercut on the projecting portion of the shaft; a sleeve positioned over the collet having an inner surface cooperating with an outer surface of the collet defined by the tongue segments and shaped to retain the projections in the undercut; and means for moving the sleeve relative to the collet in the axial direction and for releasably maintaining the collet and the sleeve in relative positions in which the projections are retained in the undercut to thereby lock the collet to the neck portion.

14. Apparatus according to claim 13 wherein the portion which projects out of the bone is angularly inclined relative to a remainder of the shaft embedded in the bone, and including a handle for applying a force to the remainder of the shaft, and means adjustably connecting the handle with the sleeve so that the application of an axial force to the elongated handle acts along a line which is substantially coaxial with an axis of the remainder of the shaft.

* * * * *